United States Patent
Pepper et al.

(10) Patent No.: US 7,212,734 B2
(45) Date of Patent: May 1, 2007

(54) PORTABLE CARBON MONOXIDE GENERATION APPARATUS FOR TESTING CO SENSORS, DETECTORS AND ALARMS

(75) Inventors: Stewart Pepper, Herts (GB); David Sharp, Hoddesdon (GB)

(73) Assignee: No Climb Products Limited (GB)

( * ) Notice: Subject to any disclaimer, the term of this patent is extended or adjusted under 35 U.S.C. 154(b) by 0 days.

(21) Appl. No.: 10/531,079

(22) PCT Filed: Oct. 9, 2003

(86) PCT No.: PCT/GB03/04384

§ 371 (c)(1), (2), (4) Date: Sep. 9, 2005

(87) PCT Pub. No.: WO2004/034051

PCT Pub. Date: Apr. 22, 2004

(65) Prior Publication Data

US 2006/0110142 A1    May 25, 2006

(30) Foreign Application Priority Data

Oct. 10, 2002 (GB) .............................. 0223608.1 U

(51) Int. Cl.
*A61H 33/08* (2006.01)

(52) U.S. Cl. ..................... 392/379; 392/386; 392/389

(58) Field of Classification Search ..................... None
See application file for complete search history.

(56) References Cited

U.S. PATENT DOCUMENTS

| | | | | |
|---|---|---|---|---|
| 4,271,693 A | * | 6/1981 | Bute | 73/1.03 |
| 4,306,575 A | * | 12/1981 | Minozzi, Jr. | 131/329 |
| 5,523,744 A | * | 6/1996 | Wieser | 340/630 |
| 6,282,940 B1 | | 9/2001 | Hung et al. | 73/1.06 |
| 6,423,962 B1 | * | 7/2002 | Pepper | 250/222.1 |

FOREIGN PATENT DOCUMENTS

DE    3721671CI    7/1988

OTHER PUBLICATIONS

"Effects of dilution on methane entering an SOFC anode" by Kendall et al., *Journal of Power Sources 106* (2002) 323-327.

* cited by examiner

*Primary Examiner*—Thor S. Campbell
(74) *Attorney, Agent, or Firm*—Renner, Kenner, Greive, Bobak, Taylor & Weber

(57) ABSTRACT

An apparatus for generating carbon monoxide comprising an enclosure (6) having an inlet and an outlet at least one of which is provided with means (8) restricting air flow from the inlet to the outlet, a container (1) located within the enclosure (6) arranged to receive carbon material (2) in intimate contact with an electrical heating element (3), and means (5) for causing air to move from the inlet to the outlet.

7 Claims, 1 Drawing Sheet

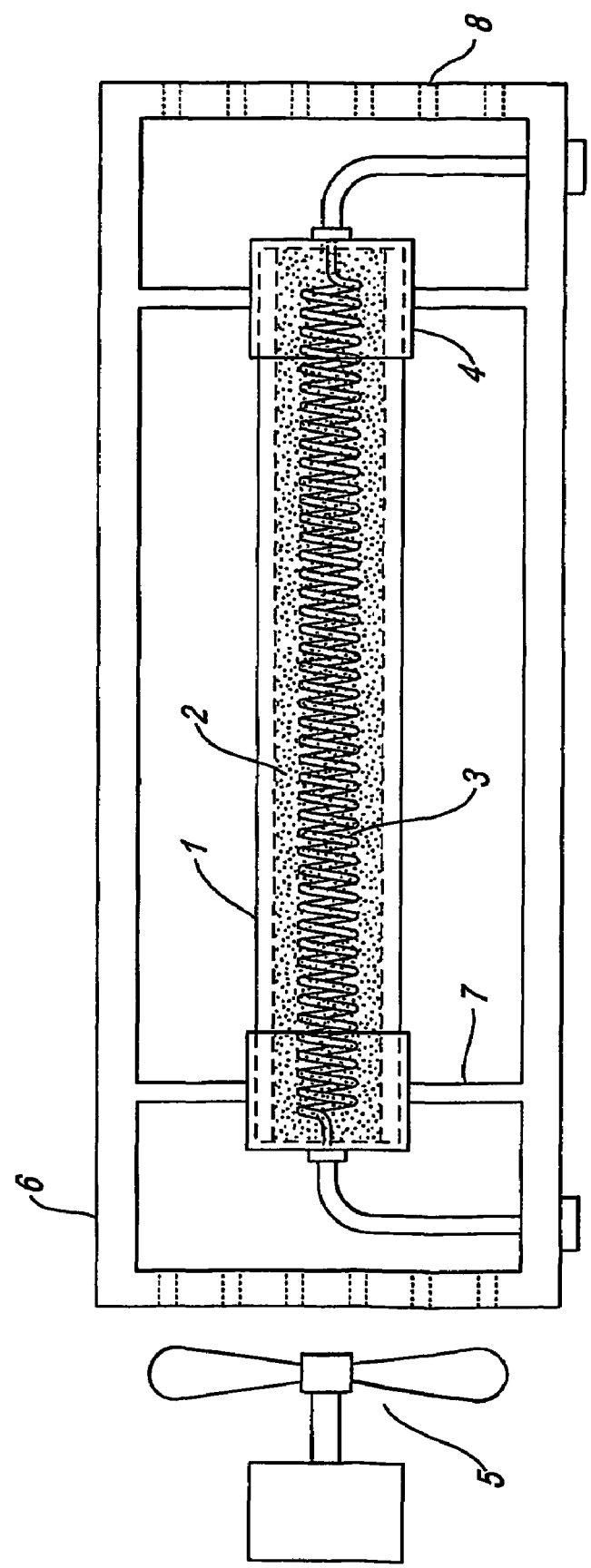

PORTABLE CARBON MONOXIDE GENERATION APPARATUS FOR TESTING CO SENSORS, DETECTORS AND ALARMS

BACKGROUND

Gas sensors that are sensitive to carbon monoxide (CO) are used in various types of alarm. The most common of these are used in installed or portable life safety alarms (industrial or residential) where elevated CO levels pose risk to health/life and in other alarms where the presence of CO is sought to be detected as indicative of other danger (e.g. fire). Examples range from gas-fired boilers, heating and cooking appliances, through personal alarms worn by workers in areas where dangerous levels of CO might be present in the atmosphere, to fire detection devices which may use CO sensors alone or in conjunction with other fire sensors such as heat and/or smoke sensors within a fire detector or system.

Certain types of CO sensors are prone to deteriorate over time, such that their performance can be effectively limited after only a few years of operation. The precise timing of their failure is not accurately predictable since it depends on factors such as the environment in which they are installed. To ensure that the sensor is operating correctly, it needs to be tested. In addition to this, CO sensors often need testing for other reasons, and the requirement to test is covered increasingly by national and international Standards.

In order to test the operation of such CO sensors, it is preferable to introduce small quantities of CO in the vicinity of the detector, at a concentration which is sufficient to activate the detector, but which, if released into the local environment is well within the safe human exposure limits. Existing methods of achieving this include the breaking of a small glass vial containing CO, and a pressurised canister containing CO diluted with air or nitrogen for example. These methods can be inconvenient and do not lend themselves very well to repeated operation with a number of sensors. They may also constitute a hazard due to the pressurisation of the canister or the concentration of the gas. Whilst some CO sensors are cross-sensitive to other gases also, testing with a stimulus of CO gas overcomes any difficulty of knowing the levels of cross-sensitivity and its variation with time, temperature, etc.

There are various methods of producing CO on an industrial scale, but these either are not suited to scaling down, or involve the use of hazardous chemicals. The present invention relates to a low power method for small-scale production of CO which can be incorporated into a small portable device for the testing of sensors. It overcomes the need to store the CO gas, uses no toxic or hazardous chemicals, and does not involve high pressures. Furthermore, this method is controllable by electrical/electronic means.

The present invention provides apparatus for generating carbon monoxide comprising an enclosure having an inlet and an outlet at least one of which is provided with means restricting air flow from the inlet to the outlet, a container located within the enclosure arranged to receive carbon material in intimate contact with an electrical heating element, and means for causing air to move from the inlet to the outlet.

Preferably, the apparatus is battery powered and also the container may be readily replaced.

In order that the present invention be more readily understood, an embodiment thereof will now be described with regard to the accompanying drawing which show a side view of an embodiment of the present invention.

The invention is based on the principle of heating carbon within an enclosure with a restricted supply of air. This will form both carbon monoxide and carbon dioxide. At a temperature of 708° C. and above the carbon dioxide will be reduced to carbon monoxide by the hot carbon. This process is used on a large scale for industrial production of carbon monoxide, but for this invention is utilised in a small low power/portable device. One embodiment of this is illustrated in FIG. 1.

A heatproof tube 1, made of ceramic, silica glass or a mica composite, of typical dimensions 50 mm long and 6 mm diameter is filled with carbon granules 2. A wire heating element 3 is included along the centre of the tube. Metal end caps 4 keep the carbon granules 2 in the tube 1 and provide electrical terminations for the element 3. The end caps 4 have a number of small holes to allow the passage of air and other gases through the tube. The tube 1 is supported within an outer casing 6 of typical dimensions 70×25×25 mm., by airtight heat-insulating bulkheads 7. A controlled amount of air is blown through the tube 1 by the fan 5.

The mixture of gases produced emerges via the holes 8 in the casing 6. In use, the fan 5 and heating element 3 are powered for a short period of typically 20 seconds to allow the carbon to reach the temperature at which CO formation becomes spontaneous, and produce sufficient for testing the operation of a CO sensor. Control of the amount of CO produced can be by control of the current and its duration applied to the element, or could incorporate a separate reference sensor for more accurate control. The restricted air flow is controlled by the fan speed, size of the holes in the end caps 4 and the size of the carbon granules, and is maintained at a value that optimises the production of CO.

The overall small size and low power nature of the device means that it may be housed in a portable instrument and powered from batteries, allowing it to be carried to the sensor to be tested.

The casing 6 and its contents can be in the form of a replaceable cartridge, to enable the efficiency of the device to be maintained should the carbon become depleted after a period of use.

Key Features.

Heating of carbon in a restricted and/or controlled atmosphere on a small scale.

Low power consumption with respect to industrial CO generation permits application to a small/portable, preferably battery-powered device.

Replaceable cartridge.

Option of control of amount of CO using a built-in sensor.

Small, safe amounts of carbon monoxide.

No hazardous materials or potentially dangerous pressures.

The invention claimed is:

1. Apparatus for generating carbon monoxide comprising an enclosure having an inlet and an outlet at least one of which is provided with means restricting air flow from the inlet to the outlet, a container located within the enclosure, said container containing a material consisting of carbon and arranged to maintain said carbon material in thermal contact with an electrical heating element, and means for causing air to move from the inlet to the outlet.

2. Apparatus according to claim 1 and further comprising a portable power supply for the electrical heating element.

3. Apparatus according to claim 2, wherein the portable power supply is one or more batteries.

4. Apparatus according to claim 1, wherein the means to cause the air to move is a fan.

5. Apparatus according to claim 2, and comprising means for controlling the amplitude or duration of the current supplied by power supply.

6. Apparatus according to claim 1, wherein restricting means comprises a baffle member provided with one or more holes.

7. Apparatus according to claim 1, wherein the container is readily removable from the enclosure so as to enable replacement of the carbon material.

* * * * *